United States Patent [19]

Lowe

[11] Patent Number: 5,409,017
[45] Date of Patent: Apr. 25, 1995

[54] MANDIBLE REPOSITIONING APPLIANCE

[75] Inventor: Alan A. Lowe, Vancouver, Canada

[73] Assignee: The University of British Columbia, Vancouver, Canada

[21] Appl. No.: 183,617

[22] Filed: Jan. 19, 1994

[51] Int. Cl.$^6$ ............................................. A61F 5/56
[52] U.S. Cl. .................................. 128/848; 128/859; 433/6
[58] Field of Search ........................ 128/848, 859–862, 128/846, 857; 433/6, 7, 18, 19, 24

[56] References Cited

U.S. PATENT DOCUMENTS

| | | | |
|---|---|---|---|
| 4,505,672 | 3/1985 | Kurz | 433/6 |
| 4,671,767 | 6/1987 | Blechman et al. | 433/19 |
| 5,066,226 | 11/1991 | Summer | 433/19 |
| 5,267,862 | 12/1993 | Parker | 128/848 |
| 5,281,133 | 1/1994 | Farzin-Nia | 433/7 |
| 5,365,945 | 11/1994 | Halstrom | 128/848 |

OTHER PUBLICATIONS

Professional Positioners Brochure May 1984.
Principles and Practice of Sleep Medicine, W. B. Saunders, 1994 "Dental Appliances for the Treatment of Snoring & Obstructive Sleep Apnea" A. Lowe Chapter 69 pp. 722–735.

*Primary Examiner*—Robert A. Hafer
*Assistant Examiner*—Michael O'Neill

[57] ABSTRACT

A mandible repositioning appliance formed by an upper bite block and a lower bite block interconnected by an adjustable mechanism including a posterior section connected to the rear portion of the upper bite block and an anterior section connected to the front portion of the lower bite block and an adjustable interconnection between the anterior and posterior sections. Preferably the adjustable interconnection will include a double thread element rotation of which changes the relative positions of the posterior and interior sections axially of the appliance and abutments to define each incremental rotation of the element. The comfort of the wearer is further improved by using a heat sensitive material in the tooth retention sections and by permitting limited relative lateral movement between the bite blocks.

4 Claims, 2 Drawing Sheets

MANDIBLE REPOSITIONING APPLIANCE

FIELD OF THE INVENTION

The present invention relates to a mandible repositioning appliance. More particularly, the present invention relates to a mandible repositioning appliance that is easily adjustable to adjust the relative position of upper and lower bite blocks and thus the position of the mandible relative to the upper jaw.

BACKGROUND OF THE PRESENT INVENTION

Repositioning appliances for positioning the mandible relative to the upper jaw as well as other devices have been used to treat afflictions such as snoring and sleep apnea.

In a paper entitled "Dental Appliances for the Treatment of Snoring and/or Obstructive Sleep Apnea" by Alan A. Lowe published in Principles and Practice of Sleep Medicine, W. B. Saunders Company, Second Edition 1994, chapter 69, p. 772–735, a number of commercially available or experimental devices known in the trade have been described together with their inherent problems and advantages.

The different techniques that have been used tend either to manipulate the tongue or adjust the relative positions of the mandible to the upper jaw.

The present invention is primarily concerned with manipulation of the mandible relative to the upper jaw to properly position the mandible to alleviate the affliction.

It will be apparent that in fitting appliances, the exact fit or degree of repositioning is obtained by trial and in incremental adjustments. Thus, in following the prior art techniques, to make a significant adjustment to the positioning of the mandible, requires dismantling and reassembling the appliance, following a relatively complex procedure normally requiring the dentist and/or his technician.

BRIEF DESCRIPTION OF THE PRESENT INVENTION

It is an object of the present invention to provide a mandible repositioning appliance that is easily adjustable and is particularly suited to treatment of snoring and sleep apnea.

Broadly, the present invention relates to a mandible repositioning appliance comprising an upper bite block, a lower bite block and an extendable connector means having a posterior section connected to said upper bite block and anterior section connected to said lower bite block and an adjustable means interconnecting said anterior and posterior sections.

Preferably said posterior section will be connected to a rear portion of said upper bite block and said anterior section will be connected to a forward portion of said bottom bite block, said forward portion being located closer to the anterior portion of the mouth of the user when the appliance is in use.

Preferably, said adjustable means is positioned substantially symmetrically relative to a longitudinal axis of said appliance.

Preferably, said posterior section will include a pair of laterally extending arms connected one to each side of said rear portion on opposite sides of the axial center line of said appliance.

Preferably, said anterior section will be connected to said front portion by a connecting means which preferably will permit limited lateral movement of said lower bite block relative to said upper bite block.

Preferably, said anterior section will include a pair of laterally spaced arms and said connecting means will comprise a separate connector for each of said arms connecting the ends of its respective arm remote from said posterior section to said front portion.

Preferably, said adjustable means will comprise a double-threaded element having one end threaded to said posterior section and the opposite end threaded to said anterior section whereby rotation of said threaded element in one direction moves said posterior and anterior section toward each other and rotation in the opposite direction move said sections away from each other.

Preferably said adjustable means will include means to prevent relative rotation of said anterior and said posterior sections.

Preferably, said adjustable means will further comprise a cooperating element engageable with said rotating element and movable in a confined passage defined in one of said anterior section or said posterior section to permit only a selected increment rotation of said rotating element and thereby preselected incremental adjustment of the relative positions of said upper and lower bite blocks.

BRIEF DESCRIPTION OF THE DRAWINGS

Further features, objects and advantages will be evident from the following detailed description of the preferred embodiments of the present invention taken in conjunction with the accompanying drawings in which.

DESCRIPTION OF THE PREFERRED EMBODIMENTS

Figure 1:
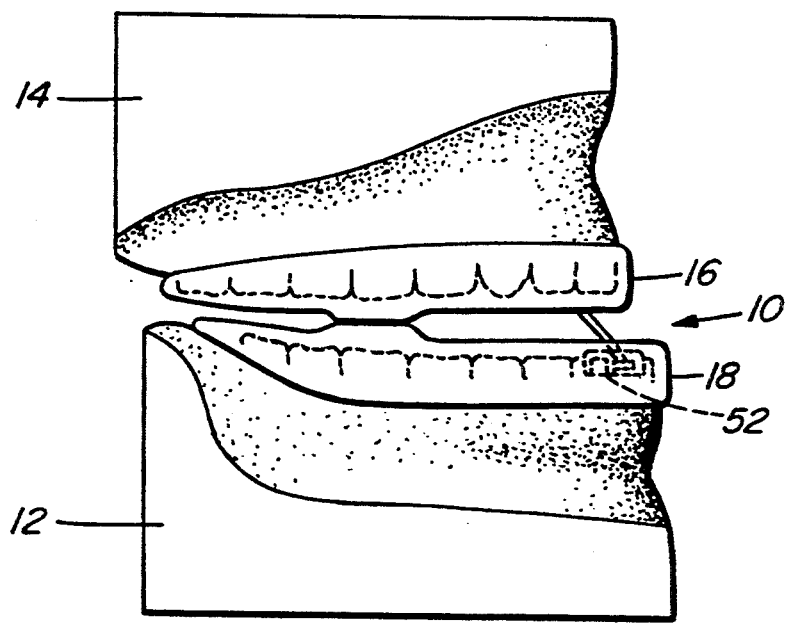
FIG. 1 is a side elevation of a model having a mandible repositioning appliance constructed in accordance with the present invention attached thereto.
Figure 2:
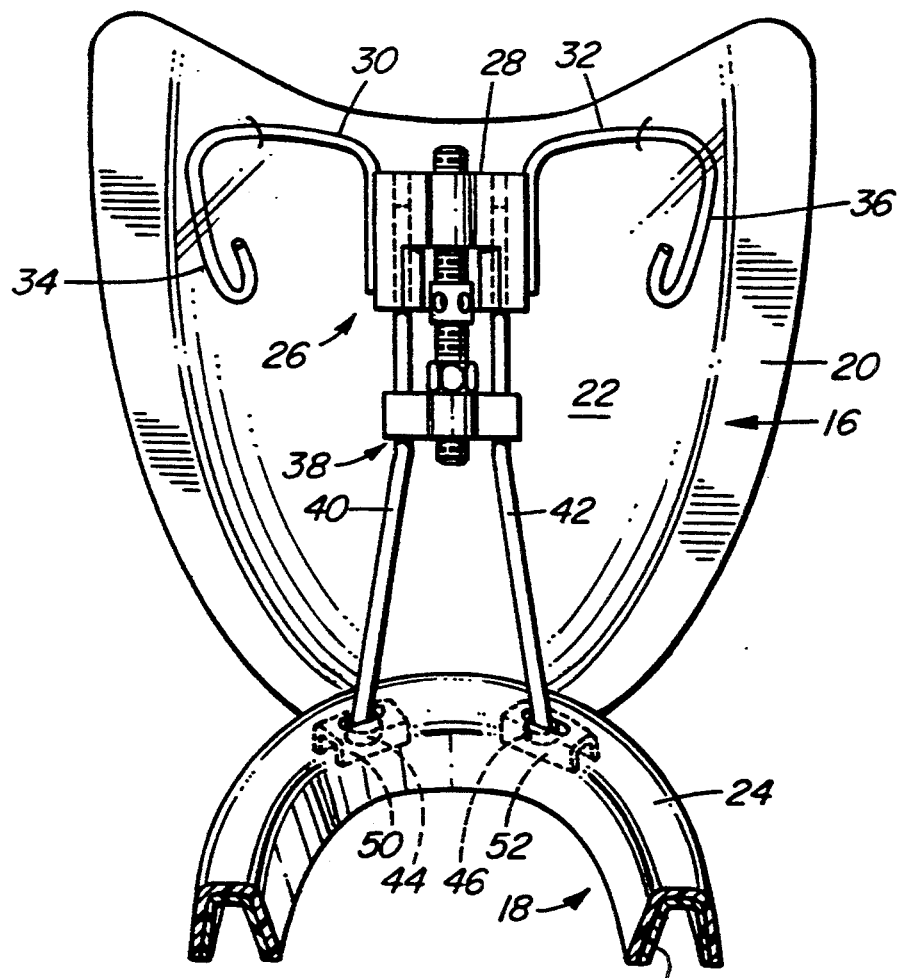
FIG. 2 is a view of the appliance in a wide opened position with the front or anterior portions of the upper and lower bite block in contact at the bottom of FIG. 2 and with the upper edge of the upper bite blocks shown at the top of FIG. 2.

As illustrated in FIG. 1, the model is formed with a model lower jaw mandible 12 and a model upper jaw 14 into which the mandible repositioning appliance 10 of the present invention is incorporated..

The mandible repositioning device 10 comprises an upper bite block 16 and a lower bite block 18.

The upper bite block 16 is provided with a U-shaped tooth retention section 20 adapted to firmly but releaseably connect the upper bite block 16 with the teeth of the user and with an upper palate 22 which bridges the gap between the sides of the U-shaped tooth retention portion 20.

The lower bite block 18 has a tooth retention section 24 similar to the tooth retention section 20 but is not provided with a bridging section interconnecting the U-shaped sides of the tooth retention section portion 24 to provide a free space for the tongue of the user.

The tooth retention sections 20 and 24 are preferably constructed from a cold-cure processed acrylic trough containing temperature sensitive elastic acrylic resin 25 (preferably the resin Clearflex® sold by Vernon-Benshoff Co.) to provide occlusal coverage of each arch. The temperature sensitive resin hardens at body temperature but is easily formable at slightly elevated temperature eg. when immersed in hot water. Preferably traditional Adam's clasps (not shown) are also incorporated to increase the retention as required.

An extendable connector 26 is composed of a posterior section 28 having an arms 30 and 32, the ends 34 and 36 of which are embedded into the material forming the upper bite block 26, thereby to firmly anchor the posterior section 28 to a rear portion of the upper bite block 16 i.e. the portion of the upper bite positioned toward the rear of the mouth when the appliance is in position in the patient's mouth.

An anterior section 38 of the illustrated extendable connector 26 comprises a pair of arms 40 and 42 having free ends 44 and 46 connected to the front portion of the lower bite block 18 (portion of the lower bite block close to the mouth opening when the appliance is in position in the mouth of the patient) via connectors 50 and 52 respectively. The interconnection between the ends 46 and 48 of the connectors 50 and 52 will be described in more detail herebelow.

Figure 3:
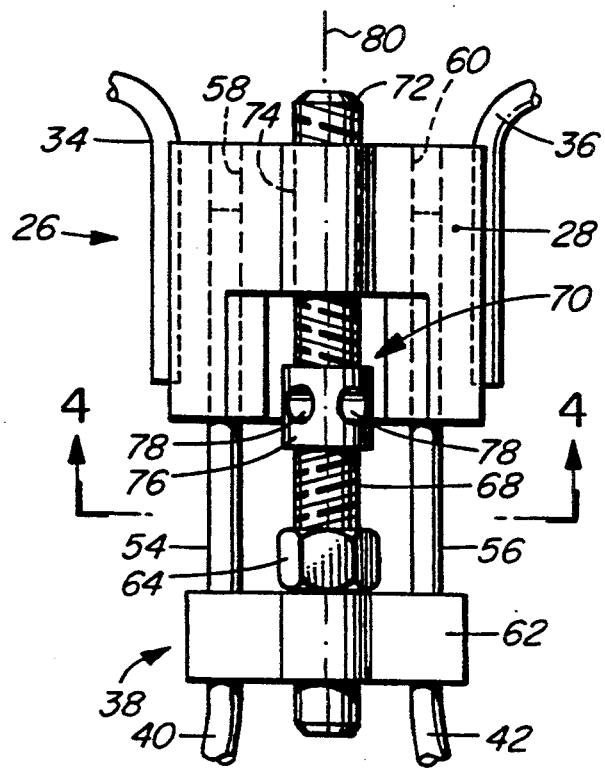
FIG. 3 is a schematic illustration of preferred form of adjusting mechanism for use with the present invention.

The anterior member or section 38 further includes rearwardly projecting parallel rod portions 54 and 56 which are received within correspond parallel guide passages 58 and 60 (see FIG. 3) in the posterior section 28. These rods 54 and 46 and their cooperating passages 58 and 60 respectively guide the relative movement of the posterior and anterior sections 28 and 38 and maintains their axial alignment and thereby the alignment of the upper and lower bite blocks 16 and 18 respectively i.e. prevent relative rotation of the anterior and posterior sections.

A bridge 62 interconnects and firmly positions the arms 40 and 42 and aligns the rods 54 and 56 with their corresponding guide passages 58 and 60.

The bridge 62 also includes a nut or threaded portion which receives one end 68 of a double-threaded adjustor which has its other threaded end 72 threadibly received in a threaded passage 74 through the anterior portion 28.

If the threaded portion 68 is a right hand thread, the portion 72 is left hand threaded a or vice versa so that rotation of the adjusting member 70 moves the posterior and anterior sections 28 and 38 relative to each other either in a direction toward each other or away from each other to adjust the spacing these sections.

In the illustrated arrangement, the adjusting member 70 is provided with an encircling angular flange 76 which, in the illustrated arrangement, is a substantially square flange having apertures 78 spaced at 90° around the axis of rotation 80 of the member 70.

Figure 4:
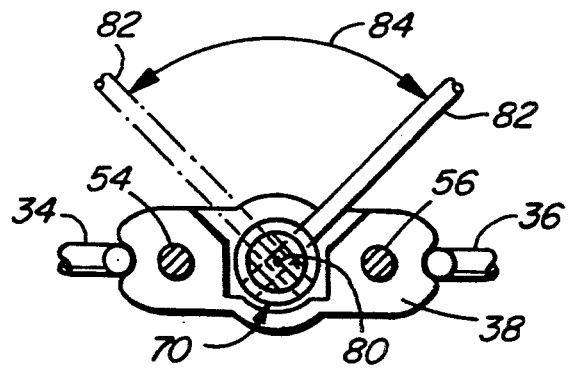
FIG. 4, section along the line 4—4 of FIG. 3, illustrating the set increment adjustment.

A removable rod such as the rod indicated at 82 in FIG. 4 is insertable into one of the apertures 78 and then rotated as indicated by the arrow 84 to rotate the member 70 and thus adjust the axial relative positions of the sections 28 and 38. It will be noted that abutments 86 and 88 formed in the posterior section 28 (or anterior section 38) are positioned on opposite sides of the flange 76 and in a position to interact with the lever 82 to limit the angular movement of the adjustor 70 with a preselected direction of rotation of the lever 82 in anyone of the holes 78. Thus, by inserting the lever 82 into the hole 78 on the left in FIG. 4, i.e. dash line position of the lever 82 and rotating it to the solid line position, the maximum rotation of the adjustor 70 is 90°. To make a further 90° adjustment in the same direction requires removal of the rod 82 and reinsertion into the next hole 78 which will be exposed in the dash line position so that preselected increments of axial movement are easily measured and obtained. In a typical embodiment of the connector 26 each 90° rotation of the member 70 result in 0.225 millimeter relative axial movement between the anterior section 38 and the posterior section 28.

One suitable expandable connector 26 for use in the present invention is a sold by Dentaurum under the trademark Hyrax® Expansion Screws. The model 602-813 has been used successfully and found to provide the required adjustment.

Figure 5:
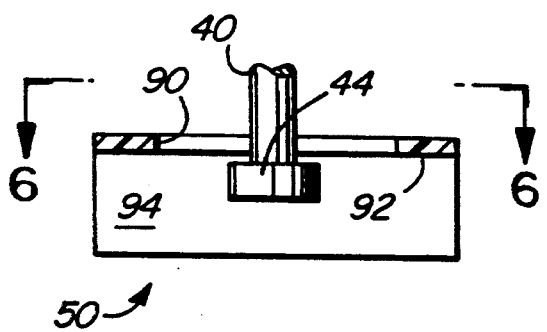
FIG. 5 is a section through the connector connecting the anterior section of interconnecting device for connecting the anterior section of the extendable connector to the bottom bite.
Figure 6:
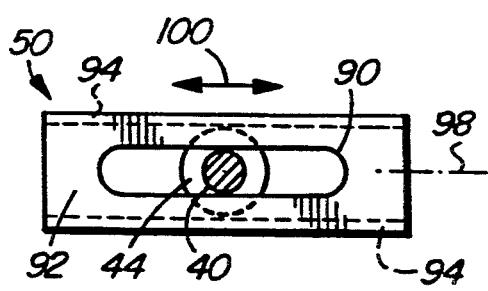
FIG. 6 is a section along the line 6—6 of FIG. 5.

The anterior arms 44 or 46 are connected to by their respective connectors 50 and 52 to opposite sides of the front portion of the bottom bite 16. Each of the connectors 50 and 52 are essentially the same and thus only the connector 50 will be described in FIG. 5.

As can be seen, each of the connectors 50 (52) is substantially in the form of a channel or U-shape formed by a bridging portion 92 and arms 94 one projecting from each side of the bridging portion 92. An elongated slot 90 having its longitudinal axis substantially parallel to the longitudinal axis of the connector 50 (52) is centrally located in and extends through the bridging portion 92.

The free end 44 (46) of the arm 40 passes through a slot 90 and is provided with a retaining enlargement 96 that prevents the free end 44 from being pulled up through the slot 90, i.e. the enlargement 96 is contained between the side walls 94 and bridging wall 90 of each of the retainers or connecters 50 (52).

The connector 50 (52) is embedded into the lower bite block 18 to secure the free end 44 (46) of the arm 40 (42) to front portion of the lower bite 18.

The connector 50 (52) is mounted to the bite block 18 in a position so that the longitudinal axis 98 of elongated slot 90 extends in a direction substantially perpendicular to the longitudinal axis 80 of the appliance 10.

When the connector 50 (52) is mounted in the bite block 18 care is taken to ensure that the free end 44 (46) and its retainer 96 are free to move along the inside of the U-shaped connector 50 (52) thereby to permit limited lateral movement of arm 40 along the slot 90 i.e. axis 98 as indicated by the arrow 100 which permits movement of the bottom bite 18 relative to the top bite block 16 which adds to the comfort of the user as it better permits coughing, speech, stretching, etc. The limited lateral movement will be in the order of 2.5 to 5 mm., preferably about 3 mm.

The use of separated arms 42 and 40 so that the connectors 50 and 52 may be laterally spaced on opposite sides of the longitudinal axis 80 of the appliance improves the stability. If desired the two ends 40 and 46 could easily have been connected together and a single coupling member 50 (or 52) used to connect the single end to a location on the front portion of the lower bite block 18 positioned along the longitudinal axis 80 of the appliance 10.

In use, after the adjusting mechanism has been set to provide a selected degree of offset of the bottom bite block 18 relative to the top bite block 16, appliance 10 is donned by the patient with the upper bite block 16 firmly fixed to the upper jaw and the lower bite block 18 firmly fixed to the lower jaw or mandible so that the upper and lower jaws are positioned in a preselected relationship depending on the adjustment of the adjustor 70.

It is an easy matter for the patient or the dentist to make a preselected adjustment to the relative position of the upper and lower bite blocks 16 and 18 by removing the appliance 10 and rotating the adjustor 70 the required number of turns in the required direction to obtain desired repositioning of the lower bite block 18 relative to the upper bite block 16. Generally these incremental adjustments are repeated until the desired objectives are attained, eg. the desired improvement (reduction) in snoring and/or sleep apnea are/is attained.

The appliance 10 via its use of temperature sensitive material, limited lateral movement and its ability to conveniently make small incremental adjustment in the relative position of the lower jaw relative to the upper jaw improves significantly the wearer's tolerance to wearing the appliance relative to other similar appliances.

Having described the invention, modifications will be evident to those skilled in the art without departing from the scope of the invention as defined in the appended claims.

I claim:

1. A mandible repositioning appliance comprising an upper bite block, a lower bite block and selectively extendable connector means having a posterior section and an anterior section interconnected by a selectively axially adjustable connector means selectively adjusting relative positions of said anterior and posterior sections along a longitudinal axis of said appliance, said posterior and anterior sections being substantially non axially extendable relative to said longitudinal axis, means connecting said posterior section to a rear portion of said upper bite block, said means connecting including a pair of laterally extending arms connected one to each side of said rear portion on opposite sides of said longitudinal axis of said appliance, connecting means connecting said anterior section to a forward central portion of said bottom bite block, said forward portion when said appliance is in position in a user's mouth being positioned closer to the anterior portion of said mouth than said rear portion of said upper bite block, said selectively extendable connector means positioned substantially along and adjacent to said longitudinal axis of said appliance and including means to substantially prevent relative rotational movement of said anterior and posterior sections about said longitudinal axis and to substantially relatively fix positions of said forward and rear portions of said lower and said upper bite blocks respectively axially of said longitudinal axis as defined by adjustment of said selectively axially adjustable connector means, said axially adjustable connector means including a double-threaded rotatable element having one end threaded to said posterior section and its opposite end threaded to said anterior section whereby rotation of said threaded element in one direction moves said posterior and anterior section toward each Other and rotation in the opposite direction moves said sections away from each other and means to permit limited lateral movement of said lower bite block relative to said upper bite block.

2. The mandible repositioning appliance as defined in claim 1 wherein said anterior section includes a pair of laterally spaced arms and said connecting means comprises a separate connector for each of said arms connecting the free ends of its respective arm remote from said posterior section to said anterior portion.

3. The mandible repositioning appliance as defined in claim 1 wherein said selectively axially adjustable connector means further comprise a cooperating element engageable with said rotatable element and movable in a confined passage defined in one of said anterior section or said posterior section to permit only a selected increment rotation of said rotating element and thereby preselected incremental adjustment of the relative positions of said upper and lower bite blocks.

4. The mandible repositioning appliance as defined in claim 2 wherein said selectively axially adjustable connector means further comprise a cooperating element engageable with said rotatable element and movable in a confined passage defined in one of said anterior section or said posterior section to permit only a selected increment rotation of said rotating element and thereby preselected incremental adjustment of the relative positions of said upper and lower bite blocks.

* * * * *